(12) United States Patent
Park et al.

(10) Patent No.: US 11,345,887 B2
(45) Date of Patent: May 31, 2022

(54) COMPOSITION FOR PRESERVING CELLS, CONTAINING, AS ACTIVE INGREDIENTS, PLANT-DERIVED RECOMBINANT HUMAN SERUM ALBUMIN AND PLANT PEPTIDES

(71) Applicant: CEFO CO., LTD, Seoul (KR)

(72) Inventors: Hyun Sook Park, Seoul (KR); Sun Ray Lee, Seoul (KR); Jin Yup Lee, Seoul (KR); Hyun Jung Mo, Anyang-si (KR)

(73) Assignee: CEFO CO., LTD, Seoul (KR)

( * ) Notice: Subject to any disclaimer, the term of this patent is extended or adjusted under 35 U.S.C. 154(b) by 147 days.

(21) Appl. No.: 15/502,699

(22) PCT Filed: Aug. 6, 2015

(86) PCT No.: PCT/KR2015/008244
§ 371 (c)(1),
(2) Date: Feb. 8, 2017

(87) PCT Pub. No.: WO2016/021955
PCT Pub. Date: Feb. 11, 2016

(65) Prior Publication Data
US 2017/0226476 A1    Aug. 10, 2017

(30) Foreign Application Priority Data

Aug. 8, 2014   (KR) ......................... 10-2014-0102083

(51) Int. Cl.
| | | |
|---|---|---|
| *A01N 1/02* | (2006.01) | |
| *C12N 5/02* | (2006.01) | |
| *C12N 5/0735* | (2010.01) | |
| *C12N 5/0797* | (2010.01) | |
| *C12N 5/0775* | (2010.01) | |
| *C12N 5/071* | (2010.01) | |
| *C12N 5/074* | (2010.01) | |

(52) U.S. Cl.
CPC ........... *C12N 5/0606* (2013.01); *A01N 1/021* (2013.01); *C12N 5/067* (2013.01); *C12N 5/0611* (2013.01); *C12N 5/0623* (2013.01); *C12N 5/0663* (2013.01); *C12N 5/0665* (2013.01); *C12N 5/0667* (2013.01); *C12N 5/0696* (2013.01)

(58) Field of Classification Search
None
See application file for complete search history.

(56) References Cited

U.S. PATENT DOCUMENTS

| | | | | |
|---|---|---|---|---|
| 5,405,772 | A * | 4/1995 | Ponting ................ | C12N 5/0647 435/373 |
| 2005/0037330 | A1 * | 2/2005 | Fischer .................. | A61K 9/127 435/1.1 |
| 2009/0246868 | A1 * | 10/2009 | Allikmets ............ | C12N 5/0043 435/364 |
| 2015/0327537 | A1 * | 11/2015 | Lee ...................... | A01N 1/0221 435/374 |

FOREIGN PATENT DOCUMENTS

| | | | |
|---|---|---|---|
| EP | 1181865 A1 | 2/2002 | |
| KR | 10-2008-0039885 A | 5/2008 | |
| KR | 10-2011-0059832 A | 6/2011 | |
| KR | 10-2014-0041249 A | 4/2014 | |
| WO | WO-2008009641 A1 * | 1/2008 | ........... C12N 5/0037 |

OTHER PUBLICATIONS

T'Jeon ("Xeno-free plant-derived hydrolysate-based freezing of human embryonic stem cells." Stem cells and development 21.10 (2012): 1716-1725) (Year: 2012).*
Babcock ("Enhancing Performance in Cell Culture" Genetic Engineering and Biotechnology News, vol. 27, Issue 20, (2007)) (Year: 2007).*

* cited by examiner

*Primary Examiner* — Robert J Yamasaki
*Assistant Examiner* — Charles Zoltan Constantine
(74) *Attorney, Agent, or Firm* — Novick, Kim & Lee, PLLC; Jae Youn Kim

(57) ABSTRACT

The present invention relates to a composition for preserving cells and a method for preserving cells and, more specifically, to: a composition for preserving cells, containing, as active ingredients, plant-derived recombinant human serum albumin and plant peptides, wherein the composition maintains a high cellular survival rate while maintaining animal-free and xeno-free properties and is stable without changes in cellular morphology or surface expression factors in the short-term preservation of cells such as stem cells or primary cultured cells; and a method for preserving cells by using the same.

4 Claims, 15 Drawing Sheets

COMPOSITION FOR PRESERVING CELLS, CONTAINING, AS ACTIVE INGREDIENTS, PLANT-DERIVED RECOMBINANT HUMAN SERUM ALBUMIN AND PLANT PEPTIDES

TECHNICAL FIELD

The present invention relates to a composition for cell preservation, the composition containing, as active ingredients, a plant-derived recombinant human serum albumin and a plant peptide and maintaining animal-free and xeno-free properties in the short-term preservation of stem cells or primary cells at room temperature or low temperatures, and relates to a use thereof.

BACKGROUND ART

Cell therapy techniques have recently been developed that are applied to the treatment of various diseases using cells or stem cells isolated from animal tissues. Stem cells are cells that can proliferate indefinitely in an undifferentiated state and differentiate to have a specialized function and shape when specific environments and conditions are provided. Human embryonic stem cells can make a continuous self-renewal under appropriate in vitro culture conditions and have the pluripotency to differentiate into all of the cell types that make up the body. Therefore, the application range of the research results on human embryonic stem cells is expanding to a wide variety of aspects, such as: the understanding of basic knowledge of development, differentiation, and growth of the human body; the development of cell therapy products for the fundamental treatment of damages or various diseases of the human body; the screening of the efficacy for various novel drug candidates; the establishment of causes of diseases; the development of therapeutic strategies; and the like.

In general, the media containing animal serum (fetal bovine serum) are used to culture human stem cells, and in such cases, although the cells cultured in fetal bovine serum are washed with an animal serum-free solution, a considerable amount of fetal bovine serum remains in the cells and acts as a strong heterologous antigen, and the fetal bovine serum has the possibility of infecting humans with animal-originated diseases, such as rabies. Therefore, the human transplantation of the cells without confirming whether fetal bovine serum remains is prohibited in the United States. The methods for isolating mesenchymal stem cells from human bone marrow and methods for isolating mesenchymal stem cells from adipose tissues are disclosed in the literatures, Pittenger et al. (Science 284: 143-147, 1997) and van et al. (J Clin Invest 58: 699-704, 1976). The literatures disclose that α-MEM or DMEM media and 10-20% fetal bovine serum were used for cell culture. However, these media have caused a lot of safety problems in human transplantation due to the use of animal serum (fetal bovine serum). In order to overcome these, an attempt has been made to use human serum instead of fetal bovine serum in a conventional cell culture medium (Kuznetsov S A, et a., Transplantation. 2000 Dec. 27; 70 (12): 1780-7), but due to the loss of characteristics in stem cells, such as a decrease in the proliferation ability of stem cells and a decrease in differentiation potency or the promotion of the differentiation into bone cells, it is difficult to use the human serum as it is for general cell culture solutions. Recently, several xeno-free culture media have been commercialized mainly by giant global companies, and thus have attracted the attention of many researchers and stakeholders. However, the xeno-free media still have problems to be overcome, such as a lower cell growth rate than the existing medium utilizing fetal bovine serum, a limit in several passages in culture, and the deterioration in characteristics as basic stem cells, including differentiation potency.

Separately, in recent years, there has also been an increase in medical officials-led medical practices in which primary cells or stem cells are extracted from tissues and immediately transplanted into the human body, and cell therapeutic agents are actively being developed, and thus a solution in which collected cells are stored before in vivo transplantation is also one of the problems to be solved. In most previous cases, the collected cells were stored or transported at low temperatures while being immersed in a basal medium, saline solution, or buffer solution, but there have been great problems in that lots of cells died, or lost their characteristics. Therefore, in order to optimize the tissue regeneration ability of stem cells, the development of techniques for increasing the cell viability at the time of stem cell transplantation, optimizing the transplantation effect, and activating the stem cells is needed, but such development has not also been sufficient until now. Meanwhile, primary cells are the normal cells, which are primarily cultured directly by animal organizations or authorities and are immediately obtained from living cells. The primary cells have been developed as cell therapeutic agents, and are used in the production of biological drugs or the like due to an advantage of the similarity with respect to an actual biological reaction.

In order to use such stem cells or primary cells in clinical tests and cell therapeutic agents, there is a strong need for the development of cell preservatives which should not use animal-derived factors, can maintain the viability of cells and stem cells collected from tissues, can keep characteristics of undifferentiated adult and human embryonic stem cells, and have an expectation of an excellent preservative effect immediately before the transplantation into the living body. The kind and composition ratio of ingredients contained in the composition for preservation are varied depending on the kind of cells to be preserved, and thus the compositional ratio of the composition for preservation needs to be studied.

The freeze-preservation at an extremely low temperature of −196° C. is stable and safe in view of the maintenance of cell viability and characteristics, and thus such a method is used for cell preservation. The living cells have been obtained by quickly thawing frozen cells as needed. However, since the formation of ice crystals and the damage of cells due to the imbalances of ions and osmotic pressure, which essentially go with freezing and thawing, are unavoidable, the cell viability is gradually reduced depending on the period after freezing and thawing. Moreover, it is practically difficult to use such freeze-preservation for cell transport and storage for hours to days but not long-term storage.

DETAILED DESCRIPTION OF THE INVENTION

Technical Problem

For the transport and storage of cells for several hours to several days, apart from the freeze-preservation for long-term preservation, there is a method of temporarily using, as a preservative, the media used to culture animal cells. However, most of such media are basal media excluding serum or the like, or a saline solution or a buffer solution, so some media cause cell death, cell viability reduction, and cell deformation. Therefore, there is a need for studies on cell preservatives characterized by safe preservation of stem cells or primary cells while sufficiently ensuring cell survival during the storage of cells at room temperature or at low temperatures. Accordingly, a purpose of the present invention is to develop a composition for preservation, which uses animal-free and xeno-free ingredients as active ingredients and has a composition ratio effective for the storage of stem cells or primary cells at room temperature or at low temperatures.

Technical Solution

An aspect of the present invention is to provide a composition for cell preservation containing a plant-derived recombinant human serum albumin and a plant peptide as active ingredients.

Another aspect of the present invention is to provide a method for preserving cells using the composition.

Advantageous Effects

According to the composition and method of the present invention, the cell viability can be maintained at a high level even without using animal-derived factors during the short-term storage of cells at room temperature or at low temperatures, and the cells can be stably preserved without cell deformation at room temperature or at low temperatures, and therefore, the present invention can be favorably used in fields of pharmaceutical and medical industries associated with stem cells or primary cells required to have animal-free and xeno-free properties.

BEST MODE FOR CARRYING OUT THE INVENTION

Figure 1:
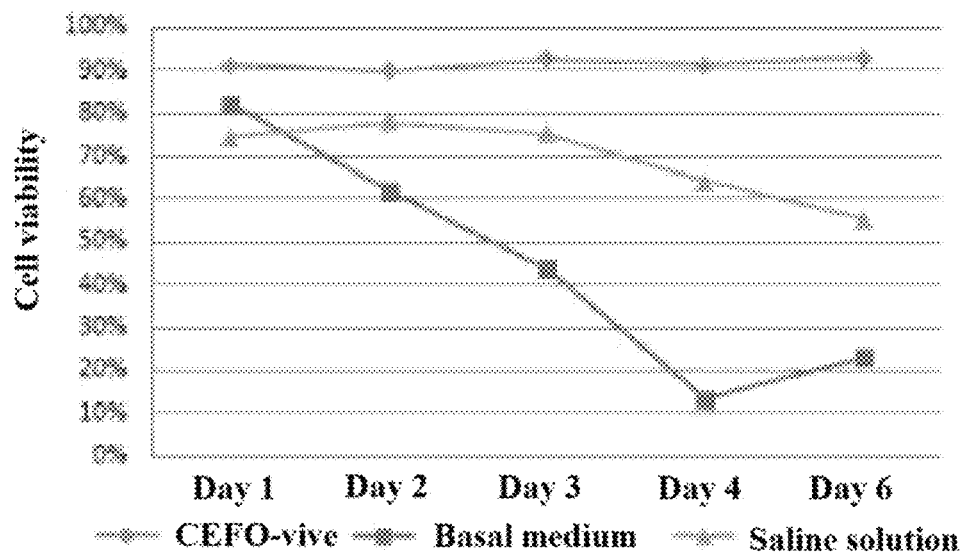
FIG. 1 is a graph confirming, through cell counting, the viability of UCMSCs over storage days after storage at a low temperature.

Hereinafter, the present invention will be described in detail with reference to the following examples. However, the present invention may be realized in various different forms, and therefore is not limited to embodiments to be described herein.

In an aspect, the present invention is directed to a composition for cell preservation containing a plant-derived recombinant human serum albumin and a plant peptide as active ingredients.

The composition for cell preservation of the present invention refers to a composition for protecting and storing cells, which are to be used before a certain experiment, operation, or treatment using cells, for several hours to several days. The composition of the present invention is different from ordinary animal cell culture media that have been used optimally for the culture and proliferation of particular cells in view of constituent ingredients, contents thereof, and a purpose of use. In other words, there is a medium optimized for each particular type of cells for the culture and proliferation of particular cells, and thus the composition for cell preservation of the present invention per se is not suitable for the use as a cell culture medium, but is merely suitable for the use as a preservation solution for increasing the cell viability when cells are stored at room temperature or at low temperatures and for preventing the deformation of cells.

In an embodiment, the composition for cell preservation of the present invention may contain 0.1-20 parts by weight of a plant-derived recombinant human serum albumin on the basis of the total 100 parts by weight of the composition.

When containing a plant-derived recombinant human serum albumin and a plant peptide as active ingredients, the composition for cell preservation of the present invention may contain, on the basis of the total 100 parts by weight of the composition, 0.1-10 parts by weight of a plant-derived recombinant human serum albumin and 0.1-10 parts by weight of a plant peptide. More preferably, the composition for cell preservation of the present invention may contain 0.5-5 parts by weight of a plant-derived recombinant human serum albumin and 1-5 parts by weight of a plant peptide. Most preferably, the composition for cell preservation of the present invention may contain 1 part by weight of a plant-derived recombinant human serum albumin and 5 parts by weight of a plant peptide.

In an embodiment, the cells may be stem cells or primary cells, and the stem cells may be umbilical cord mesenchymal stem cells (UCMSCs), adipose-derived mesenchymal stem cells (ADMSCs), or bone marrow-derived mesenchymal stem cells (BMMSCs).

In an embodiment, the composition for cell preservation of the present invention may be xeno-free and animal-free since it contains no animal-derived ingredient.

The cells for which the composition for cell preservation of the present invention can be used are animal cells. The composition of the present invention is used for, preferably stem cells, and more preferably adult stem cells. The composition for cell preservation of the present invention uses no animal factor and contains a plant-derived recombinant human serum albumin and a plant peptide, thereby maintaining the xeno-free property thereof, so that the composition can be safely used because of the low infection risk of prion proteins and the like in the preservation of stem cells or primary cells.

In an embodiment, the plant-derived recombinant human serum albumin may be derived from rice, and the plant peptide may be derived from soybean.

The composition of the present invention may further contain inorganic salts, vitamins and nucleic acids, and the minerals and vitamins can perform functions (for example, antioxidative action) in association with the role of removing toxic substances produced by cells, thereby increasing the cell viability.

As used herein, the term "plant-derived recombinant human serum albumin" refers to a protein that is obtained by the transformation of plant cells using the whole amino acid sequence of a human serum albumin or an amino acid sequence of a portion of a human serum albumin having biological activity. The human serum albumin can be used as an animal-free alternative that is equivalent or superior to the serum in the preservation of stem cells or primary cells, and can be added to the composition for the preservation of stem cells or primary cells to stabilize cells. Since an embodiment of the present invention has an advantage in that the risk of an animal or viral infectious factor can be minimized by using a recombinant human serum albumin produced in a plant (rice), the composition of the present invention has a usefulness in view of the use for stem cells or a primary cells, especially, the use as a therapeutic agent. In addition, the plant-derived recombinant human serum albumin contained in the composition of the present invention has an advantage in that it rarely exhibits lot to lot variation, unlike human serum albumins derived from animal cells or serum.

As used herein, the term "plant peptide" refers to a peptide extracted from a plant. Considering the purpose of the present invention, the plant peptide is not particularly limited as long as it contains an amino acid capable of reducing cell damage in cell preservation. In one example of the present invention, a plant peptide extracted from soybean was used. The plant peptide has a low risk of infection with prion proteins due to animal-free property thereof, maintains the xeno-free property thereof, and contains essential amino acids and/or non-essential amino acids, which can be used as basic energy sources for cells, and therefore, at the time of cell preservation, the plant peptide contributes to the increase in the cell viability by supplying nutrients to stem cells or primary cells and enhancing activity of the cells.

As used herein, the term "stem cells" refers to undifferentiated cells having self-renewal and differentiation potency. Stem cells include sub-groups of pluripotent stem cells, multipotent stem cells, and unipotent stem cells, according to their differentiation potency. Pluripotent stem cells mean cells that have the potency to differentiate into all tissues or cells constituting a living organism, and multipotent stem cells mean cells that do not have the potency to differentiate into all kinds but into plural kinds of tissues or cells. Unipotent stem cells mean cells that have potency to differentiate into particular tissues or cells. The pluripotent stem cells may include embryonic stem cells (ES cells), embryonic germ cells (EG cells), induced pluripotent stem cells (iPS cells), and the like. The multipotent stem cells may include adult stem cells, such as mesenchymal stem cells (derived from adipose, bone marrow, umbilical cord blood, or umbilical cord, etc.), hematopoietic stem cells (derived from bone marrow or peripheral blood), neural stem cells, germ stem cells, etc. The unipotent stem cells may include committed stem cells for hepatocytes, which are usually quiescent with low self-renewal capacity but vigorously differentiate into only hepatocytes after activation. In an example of the present invention, it was verified that, for bone marrow-derived mesenchymal stem cells, adipose-derived stem cells, and umbilical cord derived stem cells, the composition of the present invention can be safely and stably used in the preservation of the stem cells at room temperature or low temperatures.

As used herein, the term "primary cells" refers to cells that are isolated from a tissue extracted from an individual, without any genetic manipulation or the like, and represent functions of an organ/tissue of a living organism. Primary cells are isolated from skin, vascular endothelium, bone marrow, adipose, cartilage, or the like, and are used for studying functions of corresponding tissues and cells or as cell therapeutic agents for restoring lost tissues.

The origin of stem cells or primary cells is not particularly limited as long as the cells can be stably preserved by the composition of the present invention at room temperature or at low temperatures. Examples thereof may include cells derived from human, monkey, pig, horse, cow, sheep, dog, cat, mouse, or rabbit. The stem cells or primary cells are preferably human stem cells or primary cells, but are not limited thereto.

In an aspect, the present invention is directed to a method for preserving cells, the method comprising treating cells with the composition for cell preservation of the present invention.

In an embodiment, the cells treated with the composition for cell preservation of the present invention may be preserved at 30° C. or lower, preferably at room temperature or at a low temperature of 0° C. to 10° C., and most preferably at 4° C.

As used herein, the term "room temperature" refers to 18° C. to 27° C.

The present invention will be described in more detail through the following examples. However, the following examples are provided merely to illustrate the present invention and not to restrict the scope of the present invention.

MODE FOR CARRYING OUT THE INVENTION

Example

Preparation of Animal-Free and Xeno-Free Composition for Cell Preservation

In order to prepare a composition for preserving cells at room temperature or at low temperatures, the composition being capable of stably preserving stem cells or primary cells in a xeno-free manner, a human recombinant albumin extracted from rice (rAlbumin ACF, Sheffield Bio-Science, USA) and a plant peptide extracted from soybean (Ultra-Pep™Soy, Sheffield Bio-Science, USA) used as active ingredient were mixed with a basal medium not containing Phenol Red to prepare a composition for cell preservation, which was called CEFO-vive. In the prepared composition for cell preservation, the human recombinant albumin was used at 1 wt % and the plant peptide was used at 5 wt %. The plant peptide had an amino acid composition shown in table 1. In addition, the specific contents of inorganic salts, amino acids, vitamins, nucleic acid ingredients, and other ingredients of the composition for cell preservation, CEFO-vivo, were tabulated in tables 2, 3, 4, 5, and 6.

TABLE 1

| Amino acid composition of plant peptide | | | | | | | | | | | | | | | |
|---|---|---|---|---|---|---|---|---|---|---|---|---|---|---|---|
| | Ala | Arg | Asp | Glu | Gly | His | Ile | Lys | Met | Phe | Pro | Ser | Thr | Tyr | Val |
| mg/L | 475 | 750 | 1,275 | 137 | 550 | 250 | 600 | 1,000 | 200 | 625 | 525 | 725 | 600 | 400 | 1,800 |

TABLE 2

| Inorganic salt | mg/L |
|---|---|
| $CaCl_2$ (anhyd.) | 200.0 |
| KCl | 400.0 |
| $MgSO_4$ (anhyd.) | 98.0 |
| NaCl | 15,300.0 |
| $NaH_2PO_4 \cdot H_2O$ | 140.0 |

TABLE 3

| 아미노산(식물)a.a) | mg/L |
|---|---|
| L-Alanine | 1,390.0 |
| L-arginine•HCl | 877.0 |
| L-asparagine•$H_2O$ | 2,645.0 |
| L-aspartic acid | 1,360.0 |
| L-cysteine•HCl | 31.0 |
| L-cysteine•HCl•$H_2O$ | 100.0 |
| L-glutamic acid | 1,863.0 |
| L-glutamine | 292.0 |
| Glycine | 1,350.0 |
| L-histidine•HCl•$H_2O$ | 292.0 |
| L-isoleucine | 652.0 |
| L-leucine | 52.0 |
| L-lysine•HCl | 1,073.0 |
| L-methionine | 215.0 |
| L-phenylalanine | 657.0 |
| L-proline | 1,715.0 |
| L-serine | 1,800.0 |
| L-tryptophan | 610.0 |

TABLE 3-continued

| 아미노산(식물)a.a) | mg/L |
|---|---|
| L-tyrosine (disodium Salt) | 452.0 |
| L-valine | 1,8460.0 |

TABLE 4

| Vitamin | mg/L |
|---|---|
| L-ascorbic acid | 100.0 |
| Biotin | 0.1 |
| D-Ca pantothenate | 101.0 |
| Choline chloride | 101.0 |
| Folic acid | 101.0 |
| i-inositol | 202.0 |
| Niacinamide | 101.0 |
| Pyridoxal HCl | 101.0 |
| Riboflavin | 10.1 |
| Thiamine HCl | 101.0 |
| Vitamin B12 | 1.4 |

TABLE 5

| Nucleoside | mg/L |
|---|---|
| Adenosine | 10.0 |
| Cytidine | 10.0 |
| Guanosine | 10.0 |
| Uridine | 10.0 |
| 2'Deoxyidenosine | 10.0 |
| 2'Deoxycytidine•HCl | 11.0 |
| 2'Deoxyguanosine | 10.0 |
| Thymidine | 10.0 |

TABLE 6

| Other ingredients | mg/L |
|---|---|
| Human recombinant albumin (Plant derived) | 10,000.0 |
| D-Glucose | 1,000.0 |
| Lipoic acid | 0.2 |
| Sodium pyruvate | 110.0 |

Test Example 1

Verification on Cell Viability of Composition for Cell Preservation

Preparation of Stem Cells or Primary Cells

Umbilical cord mesenchymal stem cells (UCMSCs), adipose-derived mesenchymal stem cell (ADMSCs), and bone marrow-derived mesenchymal stem cells (BMMSCs) were directly extracted from the umbilical cord, adipose, and bone marrow that have been donated by patients, respectively. CEFOgro™UCMSC, CEFOgro™ADMSC, and CEFOgro™BMMSC media (basal media) were used as culture media for the stem cells. Human diploid fibroblasts (HDFs) were used as primary cells, and cultured in CEFOgro™HF media. These cells were cultured in an incubator under conditions of 37° C. and 5% $CO_2$, and the culture media were sustained through the replacement every 3 days. All tests of the present invention were approved by the Institutional Bioethics Review Board at CEFO Co., Ltd., and performed by procedures and methods in compliance with Bioethics and Safety Act.

Cell Counting After Low-Temperature Preservation

Figure 2:
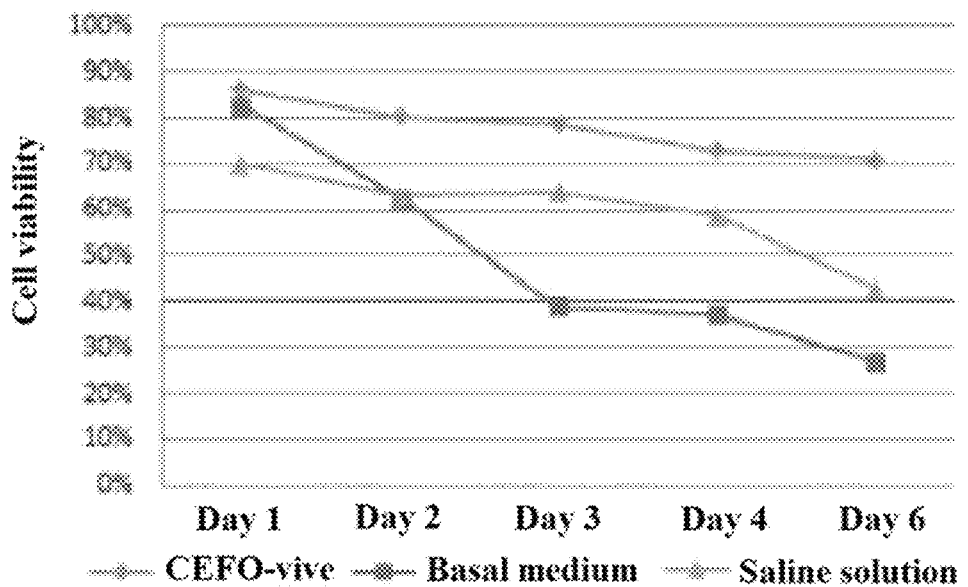
FIG. 2 is a graph confirming, through cell counting, the viability of ADMSCs over storage days after storage at a low temperature.
Figure 3:
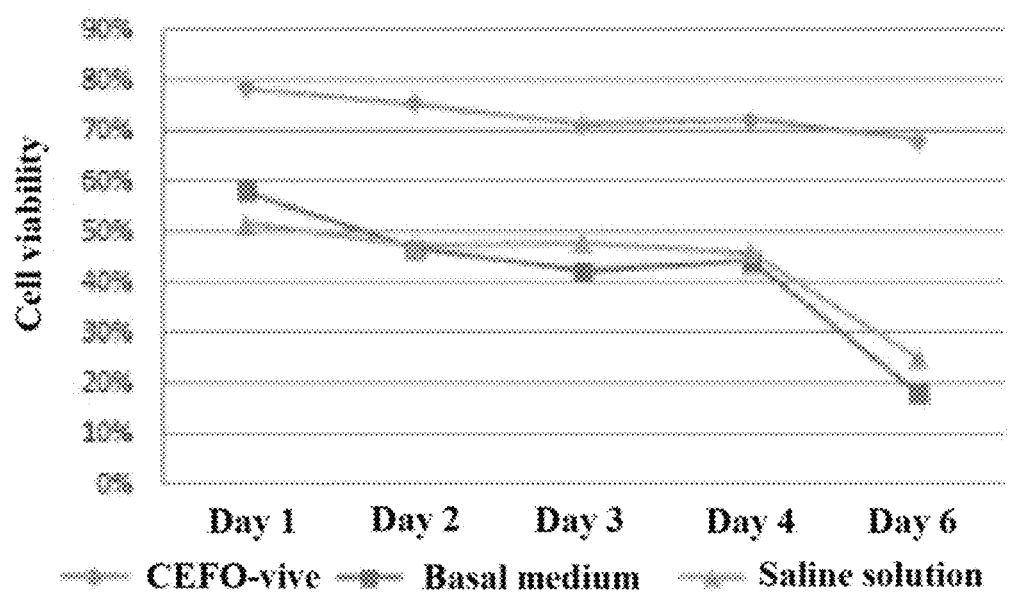
FIG. 3 is a graph confirming, through cell counting, the viability of BMMSCs over storage days after storage at a low temperature.
Figure 4:
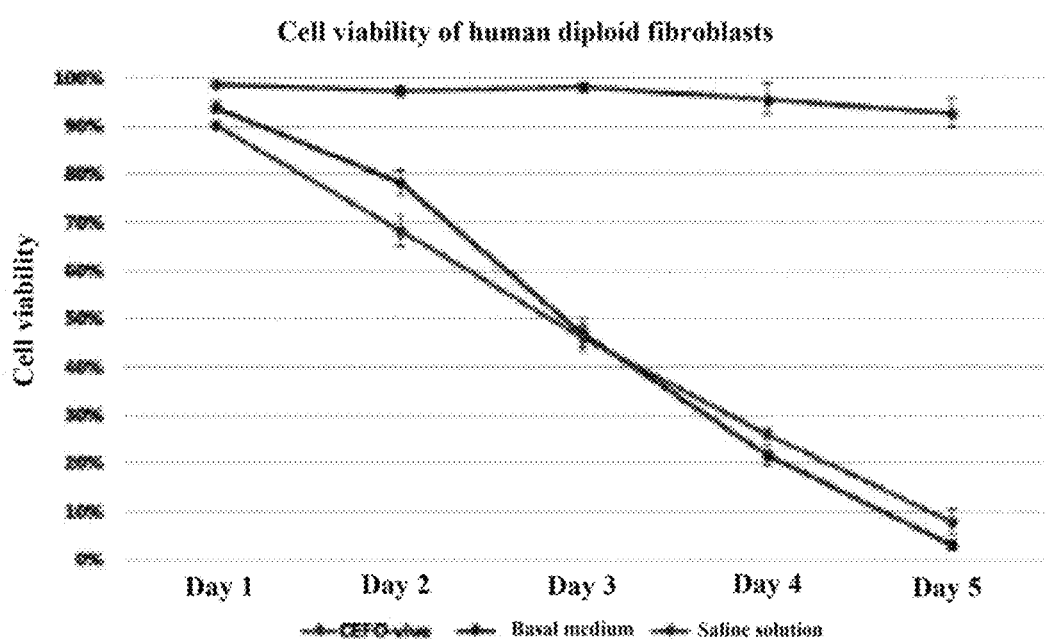
FIG. 4 is a graph confirming, through cell counting, the viability of human diploid fibroblasts (HDFs), as primary cells, over storage days after storage at a low temperature.

Stem cells UCMSCs, ADMSCs, and BMMSCs were cultured in their respective basal media, followed by treatment with trypsin, and then the cells were individually collected. The individually collected cells were put in the composition for cell preservation of the above example (CEFO-vive), a basal medium, or a saline solution, and stored in a refrigerator (4° C.). Then, cell viability was monitored by taking three vials each day to count viable cells until the 6th day of storage. The results verified that the CEFO-vive showed an average cell viability of 70% or more even on the 6th day of storage, unlike the basal medium or saline solution (FIGS. 1, 2, and 3). In addition, human diploid fibroblasts (HDFs) as primary cells were cultured in the CEFOgro™HF medium, and then treated with trypsin, followed by collection. The collected cells were put in the composition for cell preservation of the above example (CEFO-vive), a basal medium, or a saline solution, respectively, and stored in a refrigerator (4° C.). Then, cell viability was monitored by taking three vials each day to count viable cells until the 6th day of storage. The results verified that the CEFO-vive showed an average cell viability of 90% or more even on the 5th day of storage, but the cell viability was rapidly reduced from the 2nd day of storage in the basal medium or saline solution (FIG. 4).

Observation of Cells Cultured After Low-Temperature Cell Preservation

Figure 5:
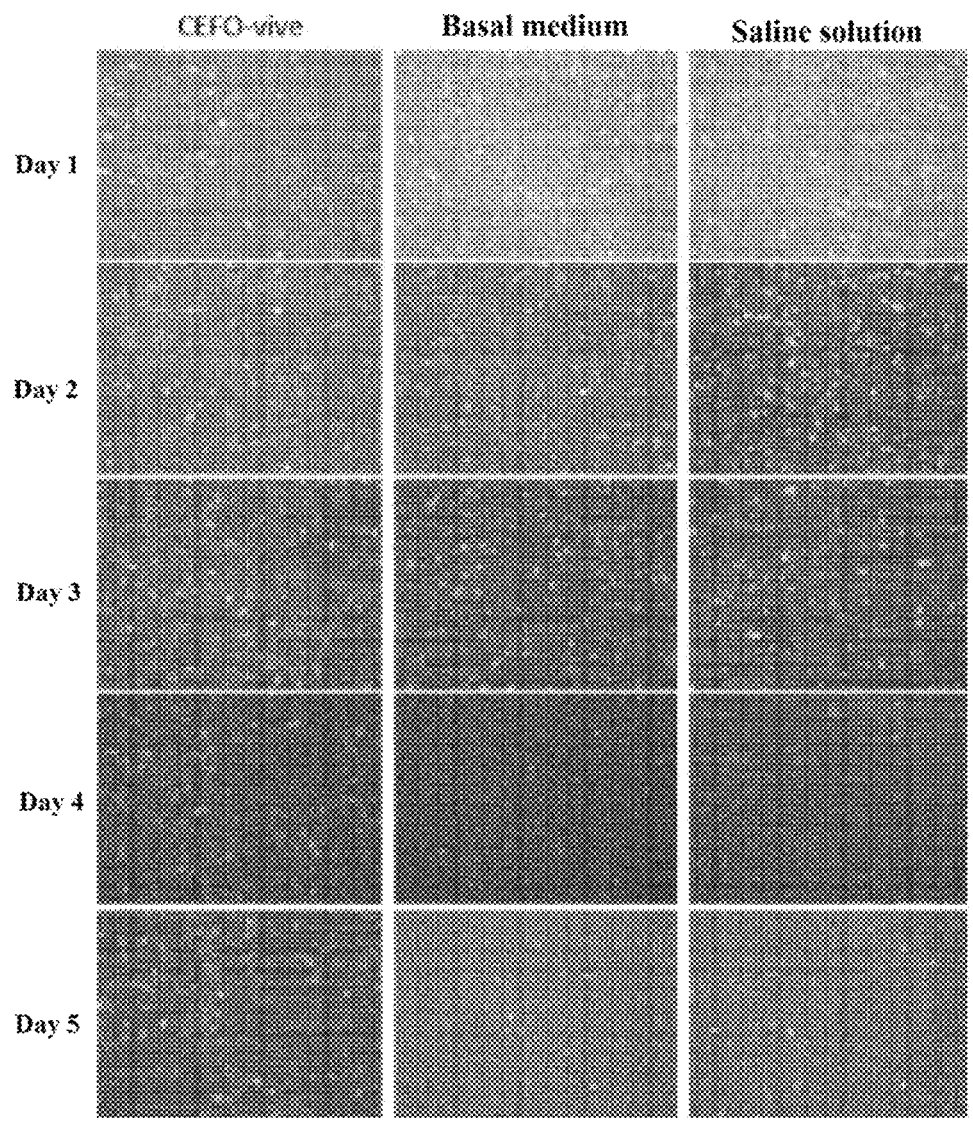
FIG. 5 shows images confirming, through a microscope, the viability and adhesive degree of UCMSCs over storage days after storage at a low temperature and re-culture for 24 hours.
Figure 6:
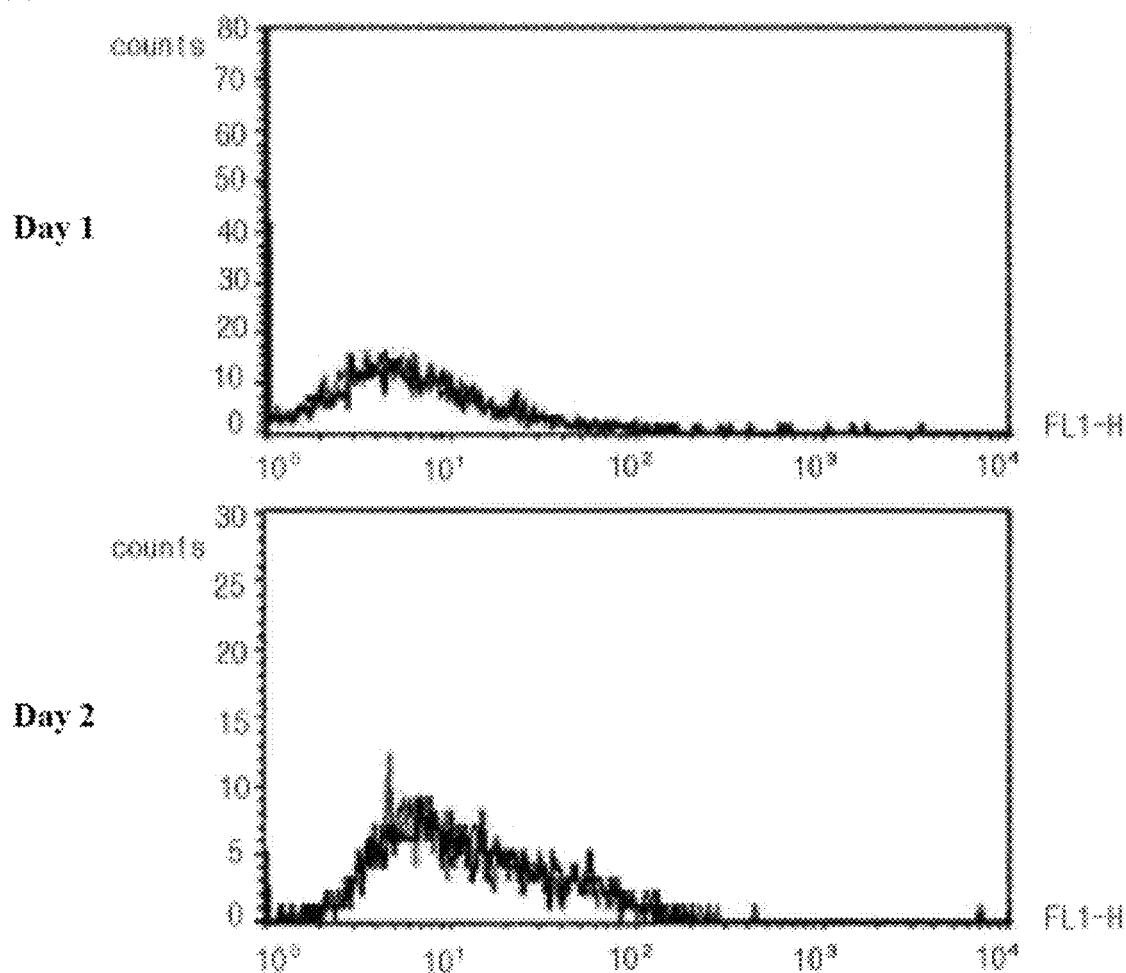
FIGS. 6 and 7 show diagrams confirming, through a flow cytometer, the change in cell surface factor CD31 of UCMSCs over storage days after storage at a low temperature while UCMSCs were treated with the composition for cell preservation (CEFO-vive) of an example of the present invention.
Figure 7:
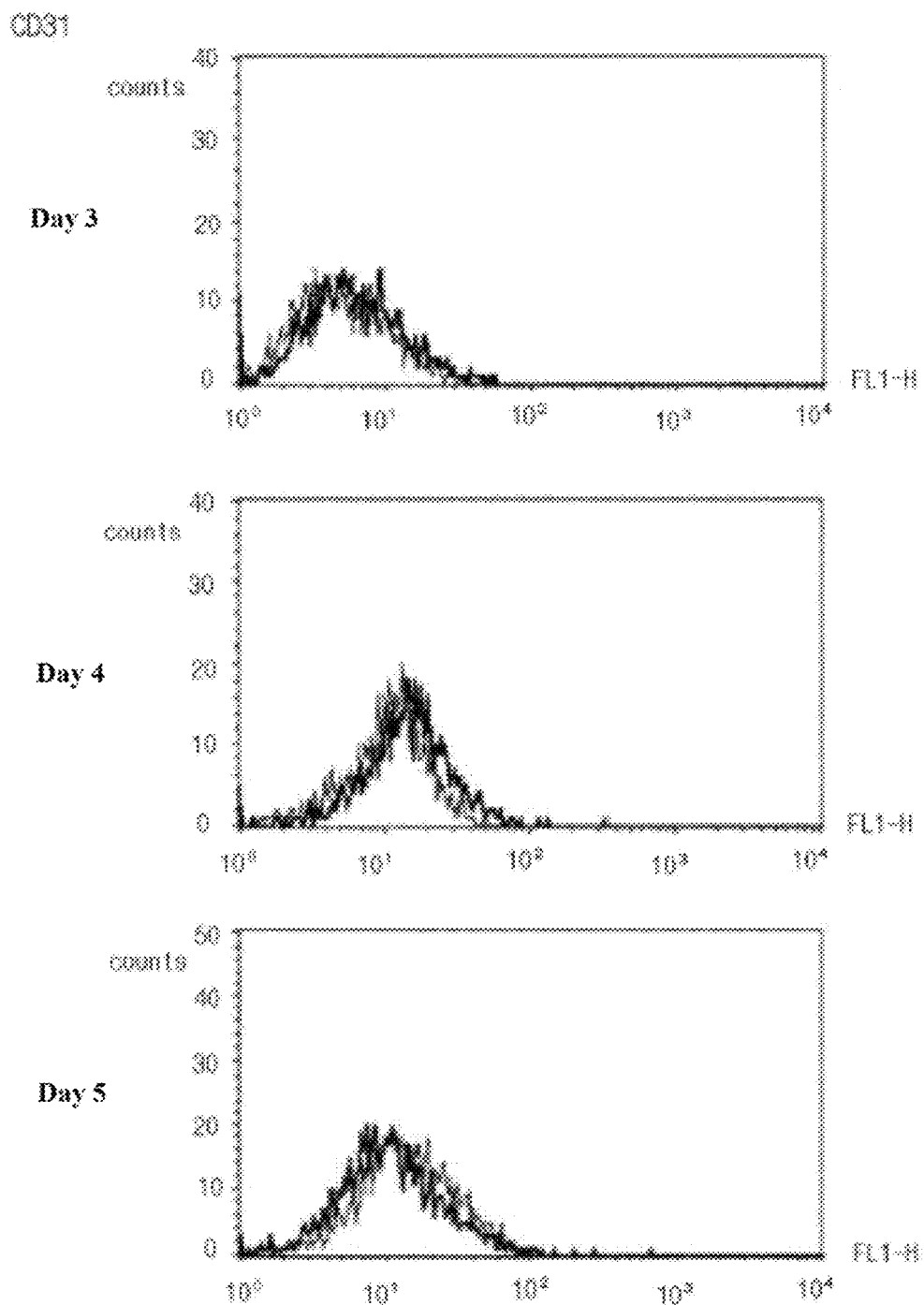
Figure 8:
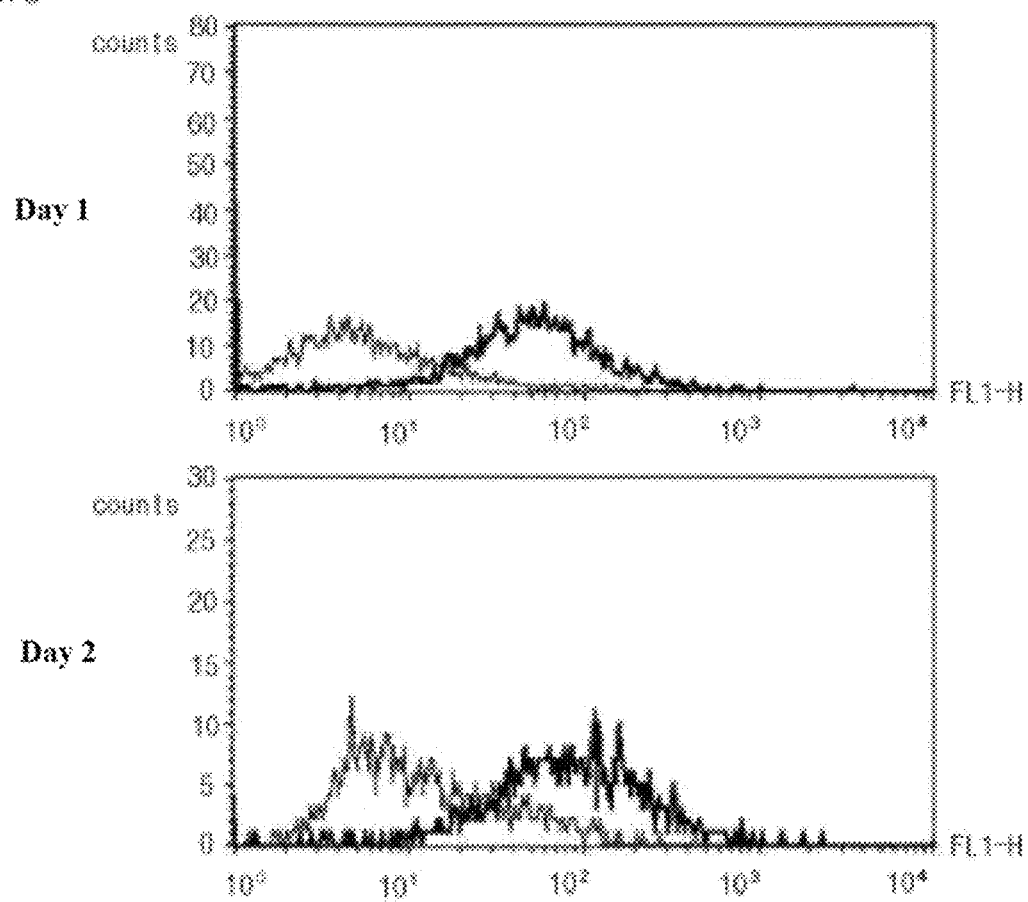
FIGS. 8 and 9 show diagrams confirming, through a flow cytometer, the change in cell surface factor CD73 of UCMSCs over storage days after storage at a low temperature while UCMSCs were treated with the composition for cell preservation (CEFO-vive) of an example of the present invention.
Figure 9:
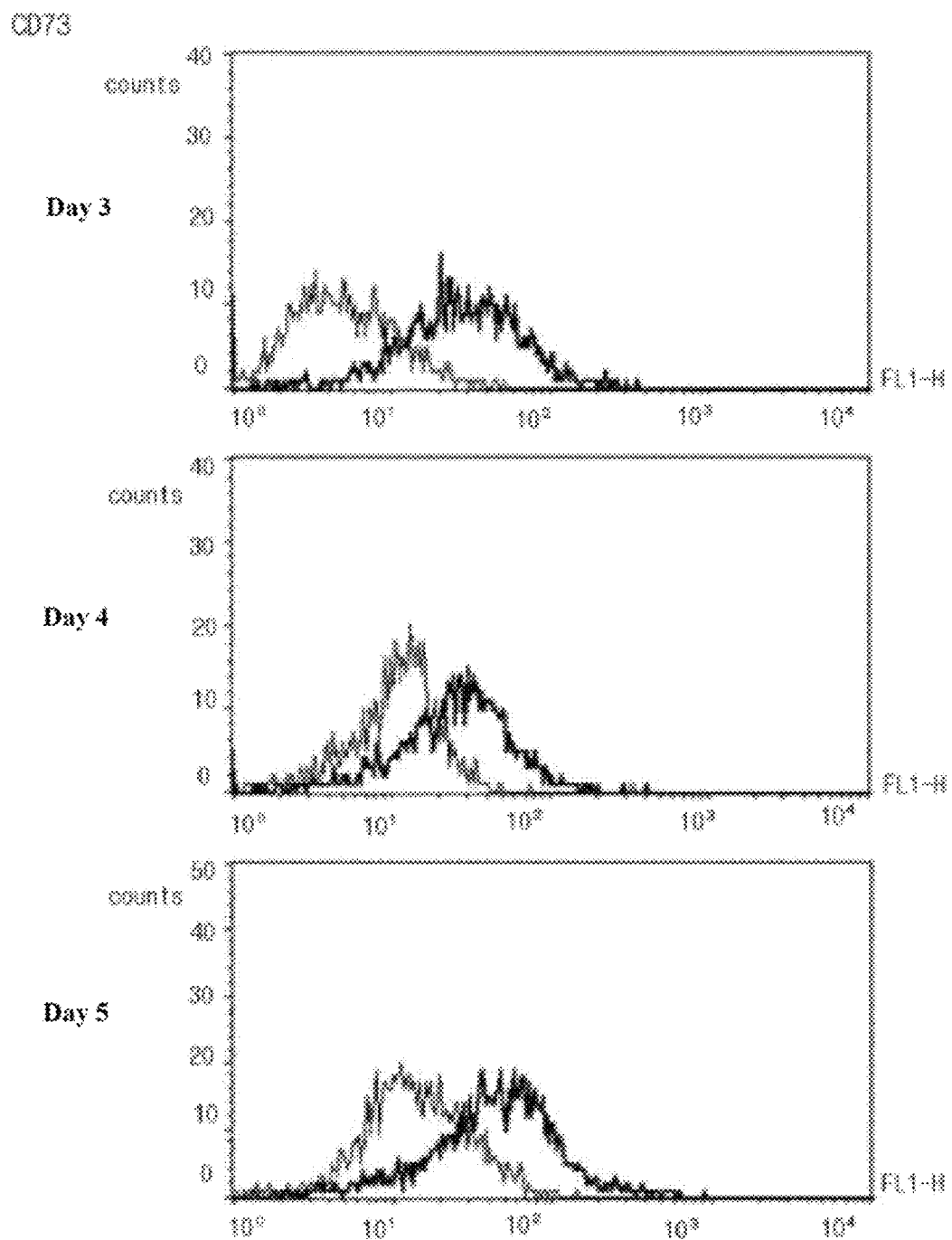
Figure 10:
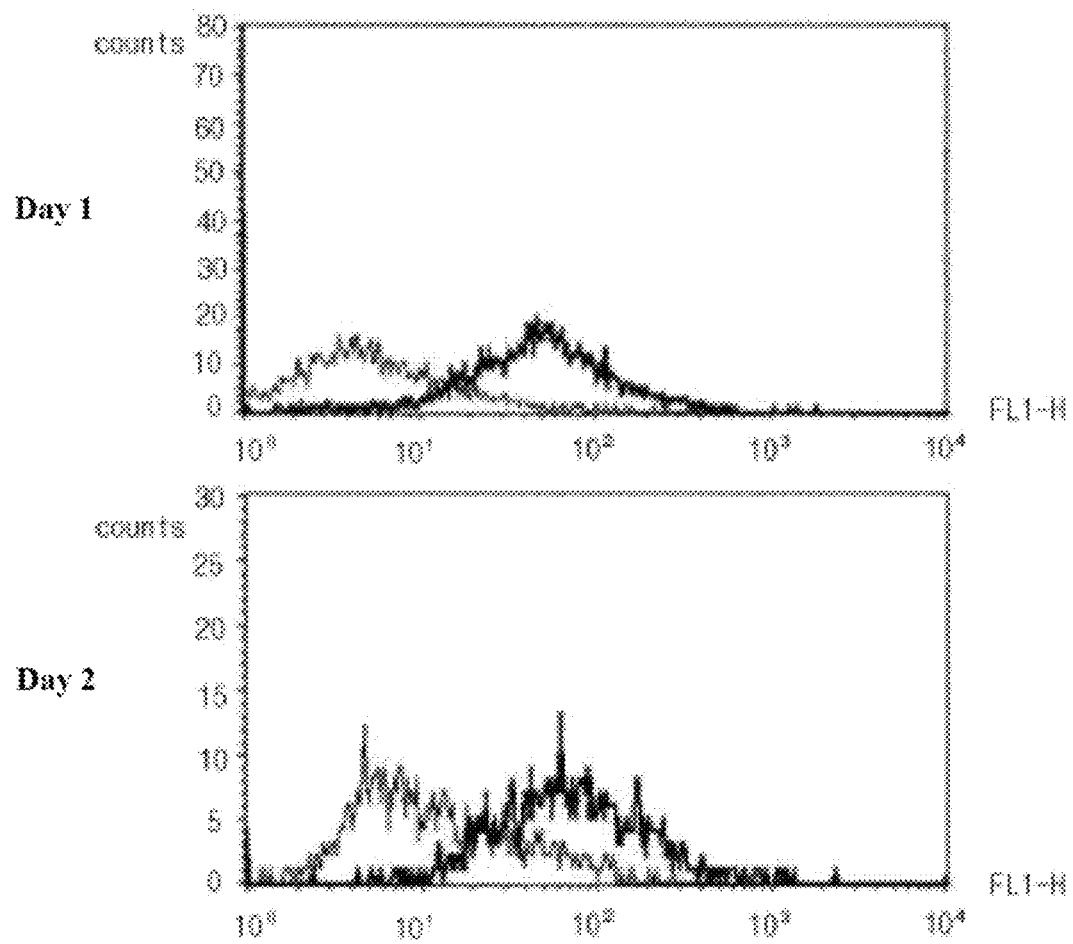
FIGS. 10 and 11 show diagrams confirming, through a flow cytometer, the change in cell surface factor CD105 of UCMSCs over storage days after storage at a low temperature while UCMSCs were treated with the composition for cell preservation (CEFO-vive) of an example of the present invention.
Figure 11:
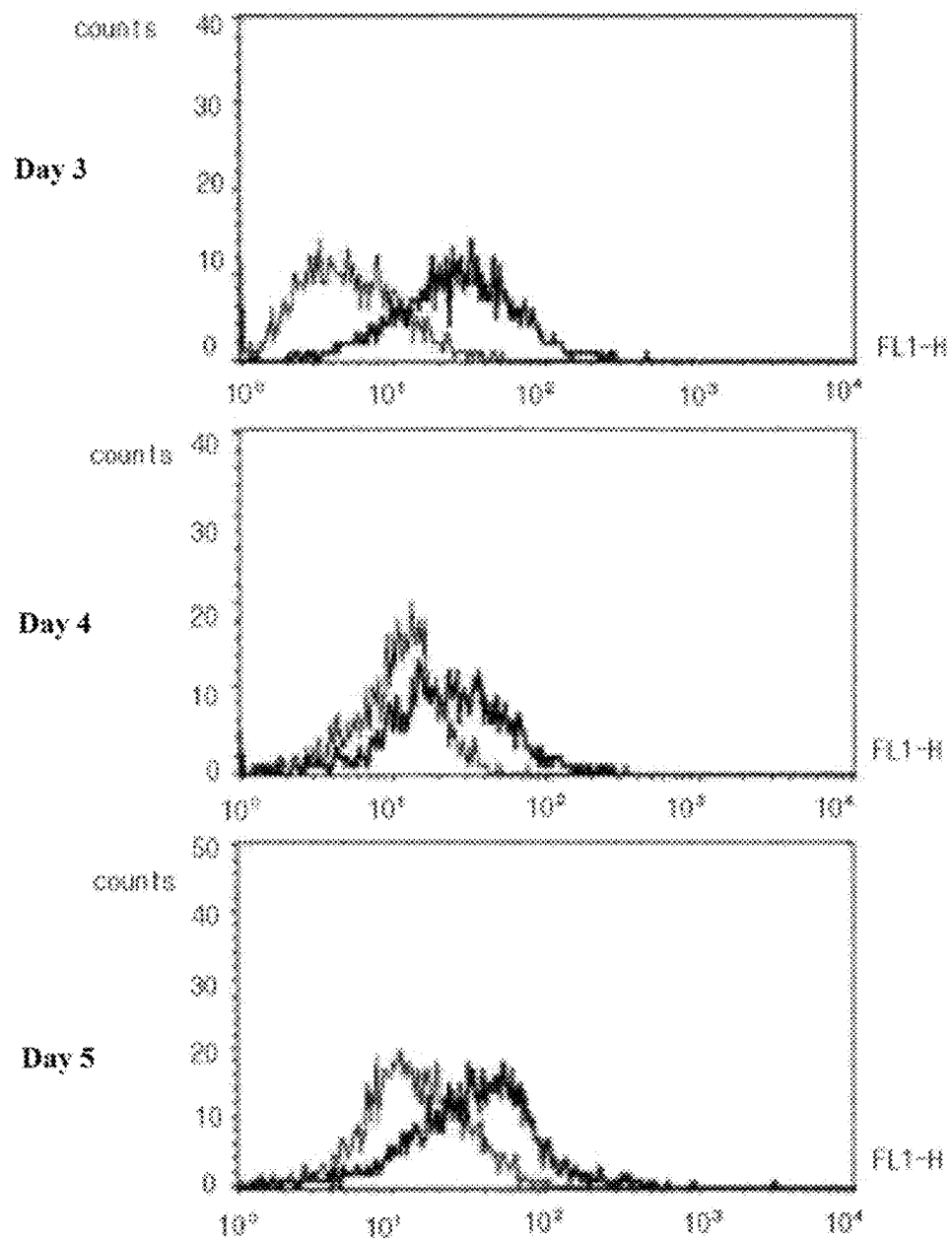
Figure 12:
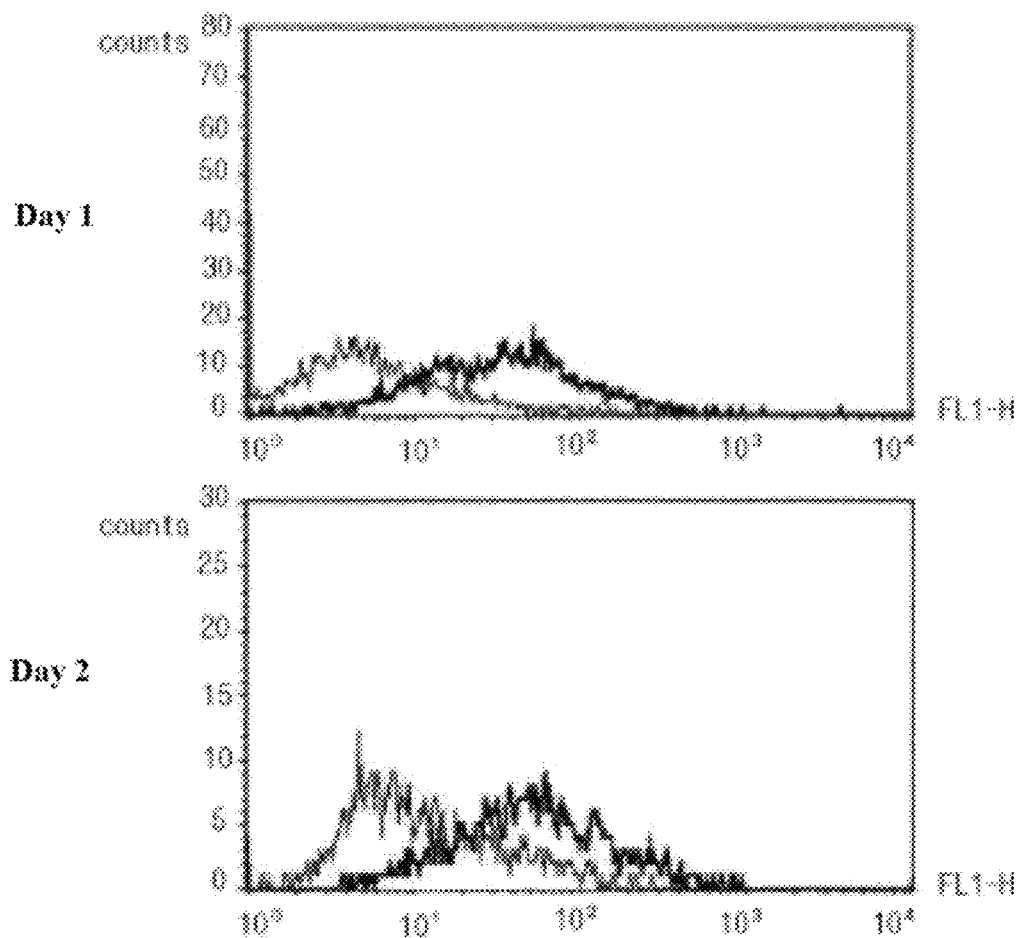
FIGS. 12 and 13 show diagrams confirming, through a flow cytometer, the change in cell surface factor CD146 of UCMSCs over storage days after storage at a low temperature while UCMSCs were treated with the composition for cell preservation (CEFO-vive) of an example of the present invention.
Figure 13:
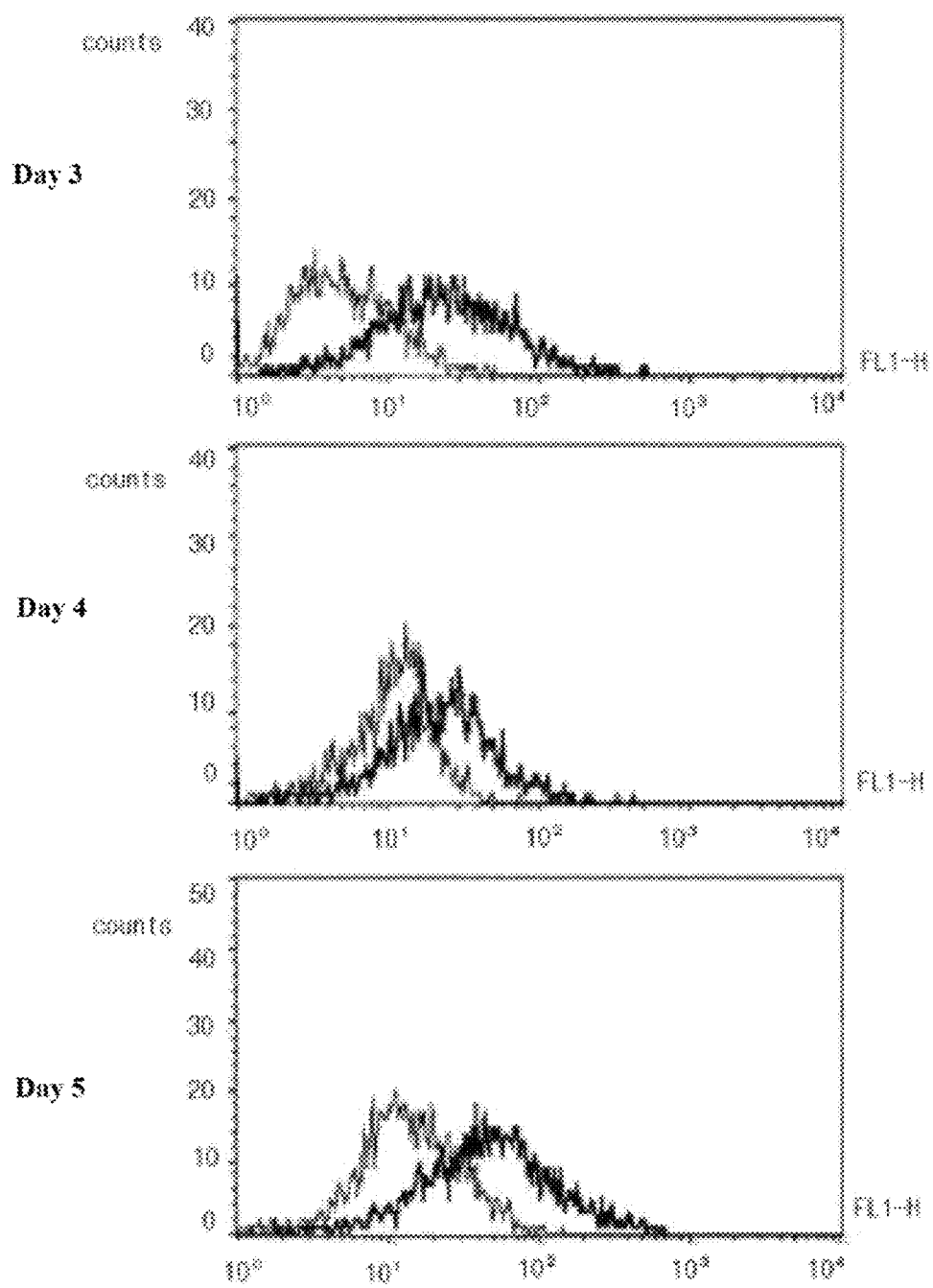
Figure 14:
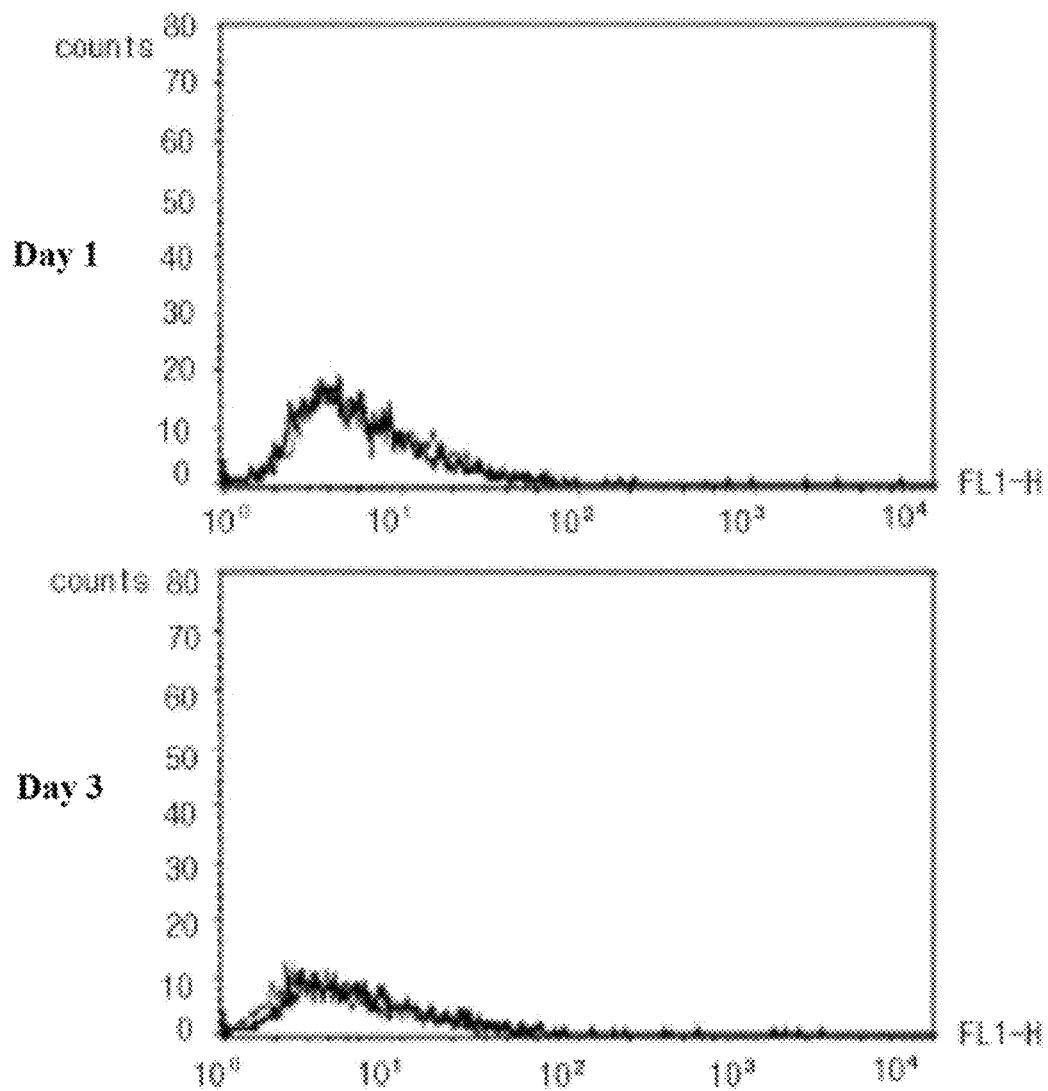
FIG. 14 shows diagrams confirming, through a flow cytometer, the change in cell surface factor CD31 of UCMSCs over storage days after storage at room temperature while UCMSCs were treated with the composition for cell preservation (CEFO-vive) of an example of the present invention.
Figure 15:
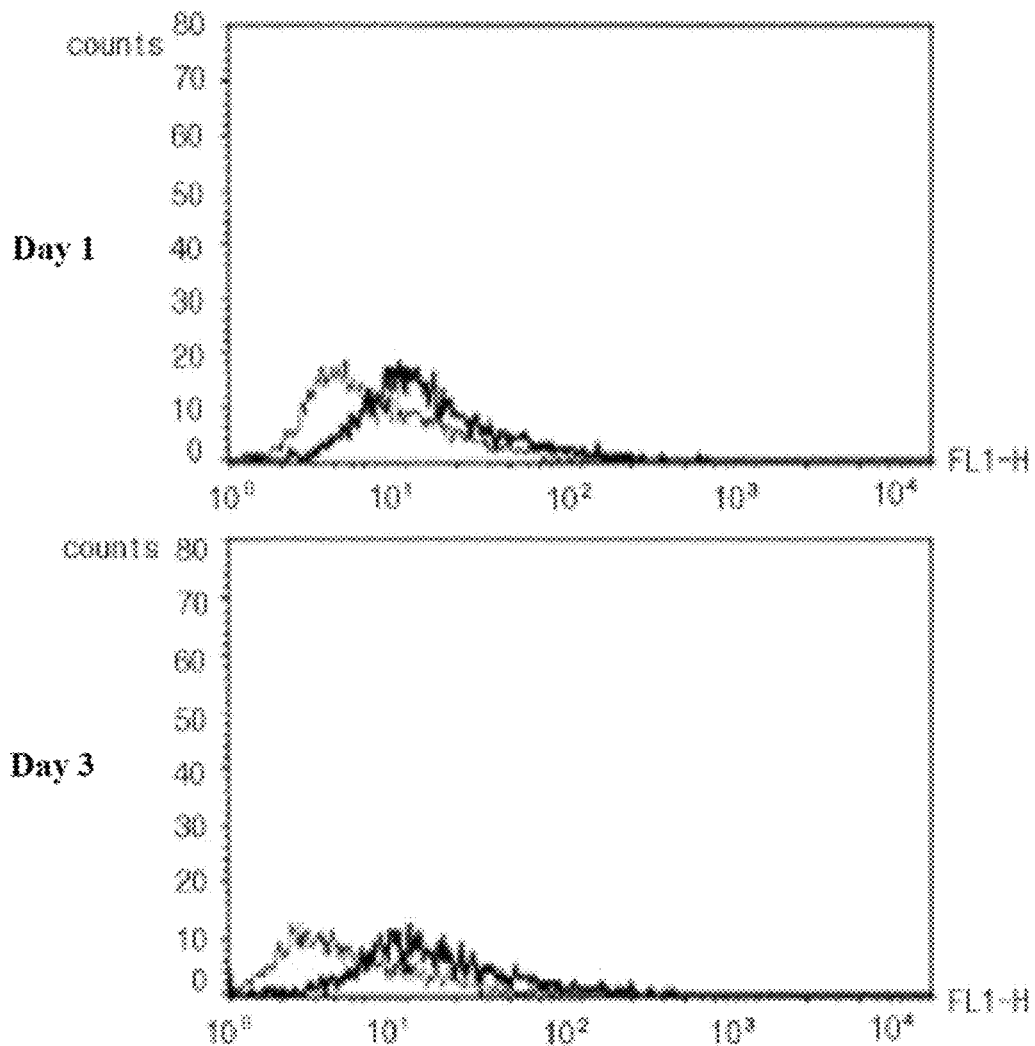
FIG. 15 shows diagrams confirming, through a flow cytometer, the change in cell surface factor CD73 of UCMSCs over storage days after storage at room temperature while UCMSCs were treated with the composition for cell preservation (CEFO-vive) of an example of the present invention.
Figure 16:
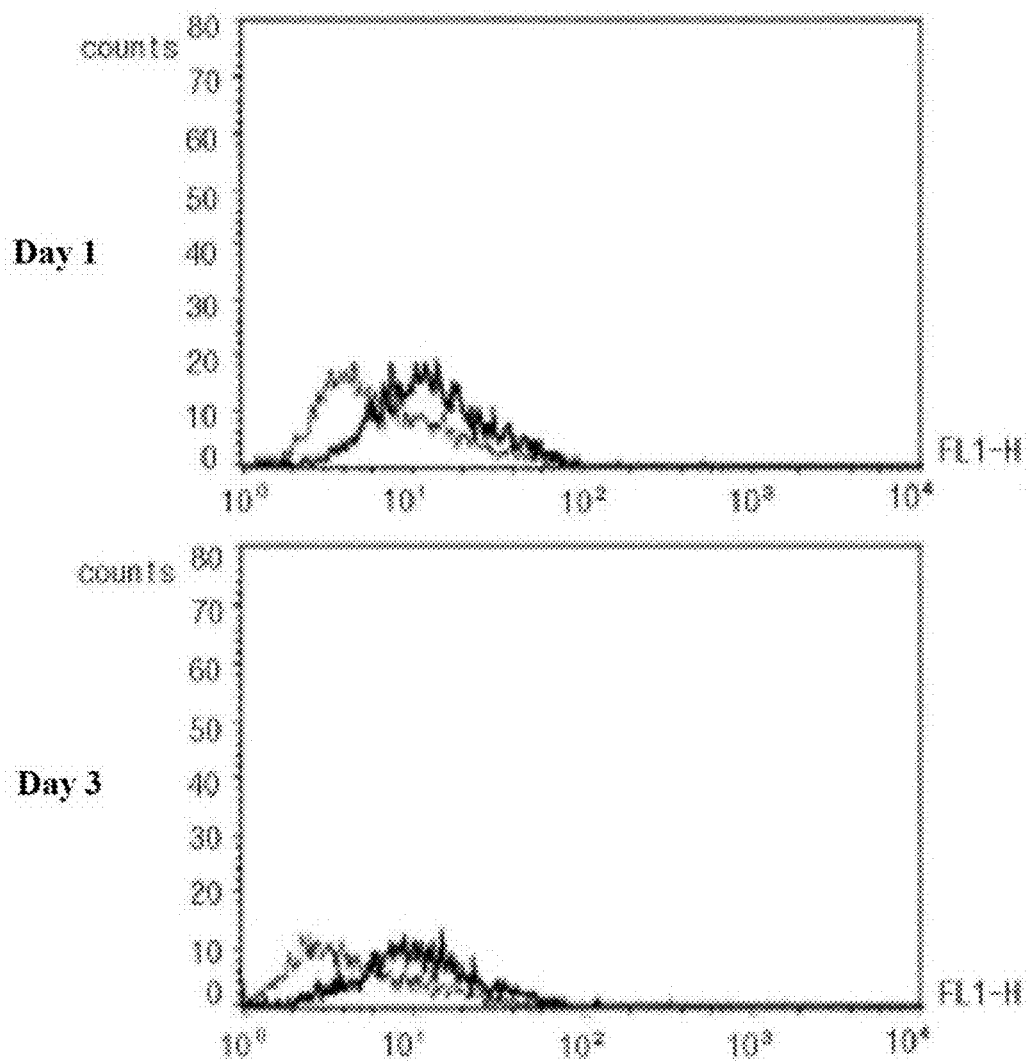
FIG. 16 shows a view confirming, through a flow cytometer, the change in cell surface factor CD105 of UCMSCs over storage days after storage at room temperature while UCMSCs were treated with the composition for cell preservation (CEFO-vive) of an example of the present invention.
Figure 17:
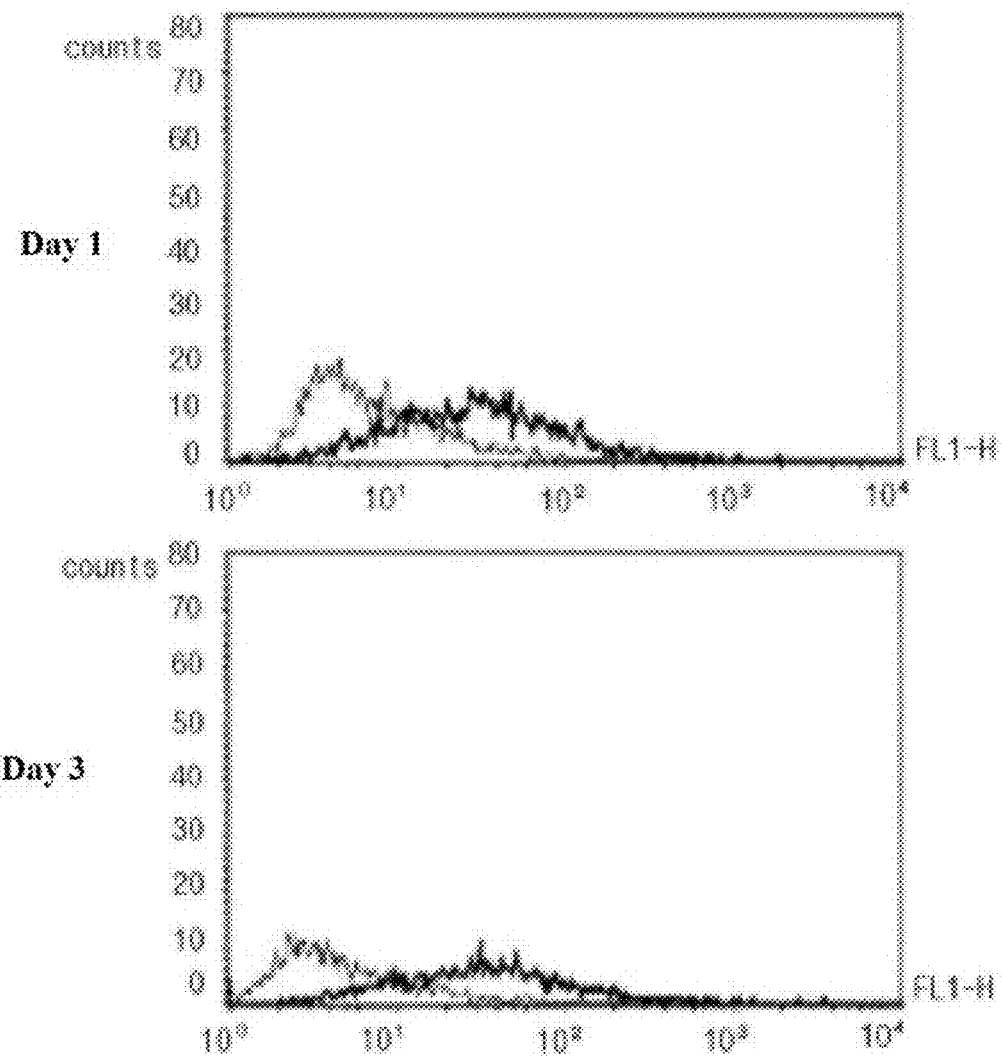
FIG. 17 shows a view confirming, through a flow cytometer, the change in cell surface factor CD146 of UCMSCs over storage days after storage at room temperature while UCMSCs were treated with the composition for cell preservation (CEFO-vive) of an example of the present invention.

UCMSCs were cultured in CEFOgro™UCMSC, and then treated with trypsin, followed by individual collection. The collected cells were put in the composition for cell preservation of the above example (CEFO-vive), a basal medium, or a saline solution, respectively, and stored in a refrigerator (4° C.). Then, three vials were taken each day, and the cells were inoculated in culture dishes and cultured in CEFOgro™UCMSC media. After cell culture for 24 hours, the cells were observed using a microscope. As a result, it was verified that, as for CEFO-vivo, the cells were favorably attached on the culture dishes at the cell re-culture even at the 5th day of storage in the refrigerated storage, but as for the basal medium or saline solution, the cells adapted poorly to the culture dishes and died from the 2nd day of the refrigerated storage (FIG. 5).

Verification on Cell Surface Factors After Low-Temperature Preservation

UCMSCs were cultured in CEFOgro™UCMSC, and then treated with trypsin, followed by individual collection. The collected cells were put in the composition for cell preservation of the above example (CEFO-vive), a basal medium, or a saline solution, respectively, and stored in a refrigerator (4° C.). Then, three vials were taken each day, and the cells were inoculated in culture dishes and cultured in CEFOgro™UCMSC media for 4 days. Thereafter, the respective cells were collected, and a flow cytometer was used to investigate the changes of CD markers (CD31, CD73, CD105, and CD146) that have been known as cell surface factors for mesenchymal stem cells. However, in the case of the cells using the basal medium or saline solution, excluding the cells preserved in CEFO-vive, the culture for 4 days could not give as many cells as can be used for analysis. Therefore, only the cell groups preserved in CEFO-vive were subjected to flow cytometry. As a result, CD31(-), CD73(+), CD105(+), and CD146(+) were shown on Day 1, Day 2, Day 3, Day 4, and Day 5, and these results indicate that there was no change in cell morphology or cell surface protein expression in the refrigerated storage of the stem cells in CEFO-vive (FIGS. 6 and 7, 8 and 9, 10 and 11, and 12 and 13).

Verification on Cell Surface Factors After Room-Temperature Preservation

UCMSCs were cultured in CEFOgro™UCMSC, and then treated with trypsin, followed by individual collection. The collected cells were put in CEFO-vive of the above example, a basal medium, or a saline solution, respectively, and stored at room temperature (25° C.). Then, three vials were taken on Day 1 or 3, and the cells were inoculated in culture dishes and cultured in CEFOgro™UCMSC media for 4 days. Thereafter, the respective cells were collected, and a flow cytometer was used to investigate the changes of CD markers (CD31, CD73, CD105, and CD146) that have been known as cell surface factors for mesenchymal stem cells. However, in the case of the cells using the basal medium or saline solution, excluding the cells preserved in CEFO-vive, the culture for 4 days could not give as many cells as can be used for analysis, in spite of room-temperature preservation. Therefore, only the cell groups preserved in CEFO-vive were subjected to flow cytometry. As a result, CD31(-), CD73(+), CD105(+), and CD146(+) were shown on Day 1 and Day 3, and these results indicate that there was no change in cell morphology or cell surface protein expression stored at the room temperature of the stem cells in CEFO-vive (FIGS. 14, 15, 16, and 17).

It can be seen from the above results that the animal-free and xeno-free composition for cell preservation of the present invention containing a plant-derived recombinant human serum albumin and a plant peptide as active ingredients ensures the cell survival and maintains the stability of cells without changing cell morphology or surface expression factors in the preservation of cells at room temperature or at low temperatures.

The invention claimed is:

1. A method for preserving animal stem cells or animal primary cells, the method comprising:
   contacting the cells with a composition for cell preservation,
   wherein the composition contains plant-derived recombinant human serum albumin and plant peptide as active ingredients, the plant-derived recombinant human serum albumin being contained at 0.5-5 parts by weight, and the plant peptide being contained at 1-5 parts by weight, on a basis of the total 100 parts by weight of the composition, and
   wherein the composition further contains $CaCl_2$KCl, $MgSO_4$NaCl, $NaH_2PO_4H_2O$, L-alanine, L-asparagine-H2O, L-aspartic acid, L-glutamic acid, glycine, L-lysine-HCl, L-proline, L-serine, L-valine, L-ascorbic acid, D-Ca pantothenate, choline chloride, folic acid, i-inositol, niacinamide, pyridoxal HCl, thiamine HCl, adenosine, cytidine, guanosine, uridine, 2'deoxyadenosine, 2'deoxycytidine-HCl, 2'deoxyguanosine and thymidine;
   and preserving the cells in the composition at 4° C. to 28° C. for 1 day to 6 days without freezing.

2. The method of claim 1, wherein the stem cells comprise umbilical cord mesenchymal stem cells, adipose-derived mesenchymal stem cells, or bone marrow-derived mesenchymal stem cells.

3. The method of claim 1, wherein the composition is xeno-free and animal-free.

4. The method of claim 1, wherein the plant-derived recombinant human serum albumin is derived from rice and the plant peptide is derived from soybean.

* * * * *